United States Patent
Brady et al.

(10) Patent No.: US 9,594,059 B1
(45) Date of Patent: Mar. 14, 2017

(54) SYSTEM AND METHOD FOR AUTOMATED BOND TESTING

(71) Applicant: The Boeing Company, Chicago, IL (US)

(72) Inventors: Steven K. Brady, Seattle, WA (US); Gary E. Georgeson, Tacoma, WA (US); Tyler M. Holmes, Seattle, WA (US); Donald D. Palmer, Jr., Berkeley, MO (US); Nathan R. Smith, St. Charles, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/985,646

(22) Filed: Dec. 31, 2015

(51) Int. Cl.
  G01N 29/04 (2006.01)
  G01N 29/265 (2006.01)
  G01N 29/06 (2006.01)

(52) U.S. Cl.
  CPC ....... *G01N 29/0645* (2013.01); *G01N 29/043* (2013.01); *G01N 29/265* (2013.01); *G01N 2291/0231* (2013.01); *G01N 2291/0289* (2013.01)

(58) Field of Classification Search
  CPC ............. G01B 12/006; G01B 29/265; G01B 2291/0231
  USPC ............................. 73/583, 602, 641
  See application file for complete search history.

(56) References Cited

U.S. PATENT DOCUMENTS

| | | | | |
|---|---|---|---|---|
| 3,534,591 A | * | 10/1970 | Phelan | G01N 29/223 73/634 |
| 7,415,882 B2 | * | 8/2008 | Fetzer | G01N 29/225 73/634 |
| 7,464,596 B2 | * | 12/2008 | Bui | G01N 29/043 73/618 |
| 9,063,059 B2 | * | 6/2015 | Na | G01N 29/0645 |
| 2002/0154307 A1 | * | 10/2002 | Bjork | G01N 21/8903 356/430 |
| 2013/0338941 A1 | | 12/2013 | Lin et al. | |

* cited by examiner

*Primary Examiner* — J M Saint Surin
(74) *Attorney, Agent, or Firm* — Thompson Hine LLP

(57) ABSTRACT

A system for automated bond testing includes a sensor that scans a material to be tested; a computer for comparing a reflected signal waveform to a plurality of signal waveforms indicating a defect in the material, and assigning a unique color to the match; a display that displays an image of the material having an assigned one of the plurality of colors indicative of a presence or absence of a defect in the test area; and an automated scanning platform that supports the sensor, the scanning platform moving the sensor in a preset motion over a surface of a test area of the material to be tested to perform an inspection scan of the material at the test area, and that positions the sensor at a predetermined position, a predetermined angle, and a predetermined contact force to acquire data consistently during an inspection.

20 Claims, 4 Drawing Sheets

SYSTEM AND METHOD FOR AUTOMATED BOND TESTING

TECHNICAL FIELD

The present disclosure is directed to non-destructive testing methods and systems, and more particularly, to methods and systems for automated testing of the bond between the components of a composite material.

BACKGROUND

Composite materials, such as fiber-reinforced composite materials, have become popular as a constituent of high-performance products and components that need to be lightweight, yet strong enough to take harsh loading conditions and stresses. Examples of such applications are components used in aerospace applications; the tails, wings, fuselages, and propellers of aircraft; boats and other marine vessels; bicycle frames; and car bodies. Modern jet aircraft include fuselages composed largely of composites. Carbon fiber-reinforced polymers (CFRPs) are used in the fuselage of aircraft and space vehicles.

One type of composite material is a lay-up comprised of a honeycomb core sandwiched between two outer skin layers above and below the honeycomb core. The entire sandwich may be made of a material such as fiberglass or a CFRP, or combinations of the two. Other forms of composite materials include a fiberglass or CFRP honeycomb core between outer skin layers of aluminum.

Such composite materials used in vehicles such as aircraft and spacecraft are subjected to shock loading, blunt and sharp impacts, repeated bending and torsional loading, and temperature extremes. Composite material may sustain damage from such use, and the damage may not be apparent from a visual inspection. For example, damage may take the form of delamination, that is, a separation between the core and outer skin of a laminate, or a crushed core, or a disbonding.

Testing is necessary to determine whether such damage has been sustained by the composite material. However, such testing must be non-destructive so that the structural integrity of the composite material to be tested must not be compromised, or compromised further, as a result of the testing. It also is desirable to test the composite structure in situ for efficiency reasons.

Consequently, non-destructive testing systems have been developed. One such system, disclosed in U.S. patent application Ser. No. 13/977,319 filed Sep. 4, 2013 and titled METHOD AND APPARATUS FOR DEFECT DETECTION IN COMPOSITE STRUCTURES, discloses a method and apparatus for defect detection in composite structures. That system and method utilize a "pitch-catch" probe connected to a control box that is controlled by a laptop computer or other computing device. The pitch-catch probe includes two transducers: a first transducer that transmits an ultrasonic signal to and through the surface of the composite material to be tested, and a second transducer that receives the ultrasonic signal. The alteration of the frequency and amplitude of the received ultrasonic signal is processed by the control box to determine the presence of a defect. Further, variations in the received ultrasonic signal may be matched with a library of known signals for that particular composite material being tested, so that the received signal can be used to determine a type of defect in the composite material.

In order to use such non-destructive inspection devices efficiently over a large area, such as may be found on an aircraft fuselage made of composite material, there is a need to provide a scanning platform that is capable of optimizing the accuracy and consistency of the data gathered by the non-destructive inspection device.

SUMMARY

The present disclosure is directed to a system and method for automated bond testing that provides a high-precision platform for data gathering by a non-destructive inspection device. In one aspect, a system for automated bond testing includes a sensor that scans a material to be tested by sending a signal to the material to be tested and receiving a signal waveform from the material indicative of a presence of a defect in the material and a type of defect present in the material; a computer in communication with the sensor for receiving the signal waveform from the material, the computer being configured to compare the received signal waveform to a plurality of signal waveforms indicating a defect in the material, and if a match exists, assign a one of a plurality of colors to the match; a display connected to receive a signal from the computer to display an image of the material to be tested having an assigned one of the plurality of colors indicative of a presence or absence of a defect in the test area; and an automated scanning platform that supports the sensor, the scanning platform moving the sensor in a preset motion over a surface of a test area of the material to be tested to perform an inspection scan of the material at the test area, and that positions the sensor at a predetermined position, a predetermined angle, and a predetermined contact force to acquire data consistently during an inspection.

In another aspect, a method for testing bonds in composite materials includes mounting on an automated scanning platform a sensor sending and receiving a signal waveform; activating the automated scanning platform such that the scanning platform moves the sensor in a preset motion over a test area of the material to be tested to perform a scan of the material; the preset motion including a predetermined position, at a predetermined angle, and a predetermined contact force to acquire data consistently during an inspection; sending a signal to the material to be tested and receiving a signal waveform from the material indicative of a presence of a defect in the material; receiving the signal waveform at a computer configured to have access to a plurality of signal waveforms, each of the signal waveforms corresponding to a different one of a plurality of types of defects in the material, and to compare the received signal waveform to the plurality of signal waveforms, and if a match exists, assign one of a plurality of colors to the match; and sending a signal from the computer to a display, the display showing an image of the test area on the material to be tested having an assigned one of a plurality of colors indicative of a presence or absence of a defect in the test area.

In yet another aspect, a method for making an automated bond testing system includes mounting on an automated scanning platform a sensor that scans the material to be tested by sending a signal to the material to be tested and receiving a signal waveform from the material indicative of a presence of a defect in the material, the support for moving the sensor in a preset motion over a test area of the material to be tested to perform a scan of the material; connecting a computer to the sensor for receiving the signal waveform from the material; programming the computer to have a plurality of stored signal waveforms, each of the stored signal waveforms corresponding to a different one of a plurality of types of defects in the material, and to compare the received signal waveform to the plurality of stored signal waveforms, and if a match exists, assign a one of a plurality of colors to the match; connecting a display to receive a signal from the computer to display a scanned image of the test area having an assigned one of the plurality of colors indicative of a presence or absence of a defect in the test area; and programming the automated scanning platform to move the sensor in a preset motion over a surface of a test area of the material to be tested to perform an inspection scan of the material at the test area, and to position the sensor at a predetermined position, a predetermined angle, and a predetermined contact force to acquire data consistently during an inspection.

Other aspects and advantages of the disclosed system and method for automated bond testing will be apparent from the following description, the accompanying drawings, and the appended claims.

DETAILED DESCRIPTION

Figure 1:
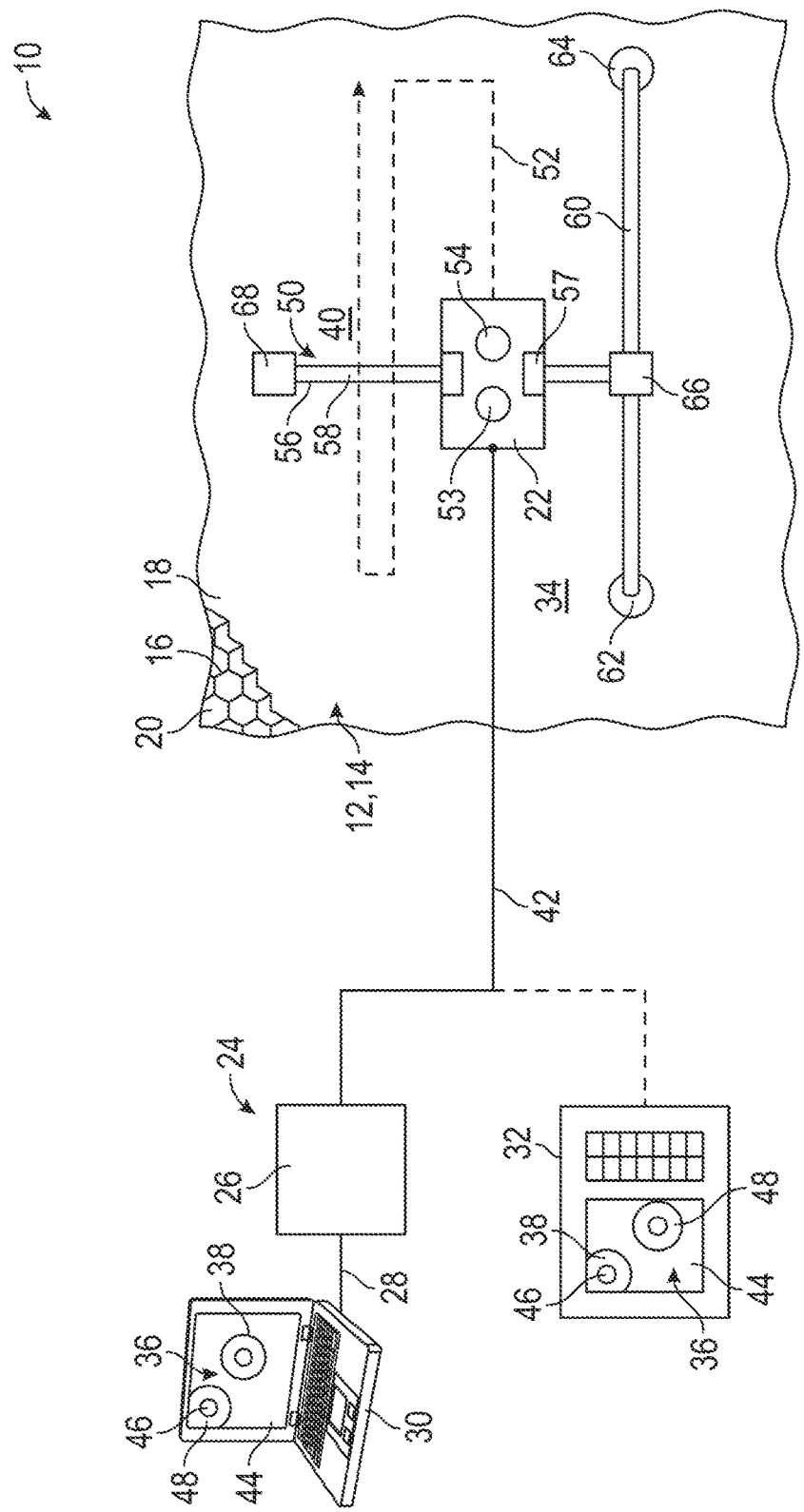
FIG. 1 is a schematic plan view of an embodiment of the disclosed system and method for automated bond testing.

As shown in FIG. 1, the system and method for automated bond testing, generally designated 10, may be used to detect defects or damage in composite material 12, which may take the form of a composite panel 14. The composite panel 14 may include a honeycomb core 16 bonded to upper and lower facings or skins 18, 20, respectively, by an adhesive. The composite panel 14 may be made of CFRP, other fiber-reinforced plastic, fiberglass, or combinations of the foregoing materials, or wholly or partly of metal. The composite panel 14 may be on, or form a portion of, a vehicle such as an aircraft, a spacecraft, a land vehicle, or a marine vehicle. The panel 14 may be a portion of the fuselage, the hull, the body, a bulkhead or other structural member, a nacelle, a cowling, or a radome.

The system 10 may include a sensor 22 that scans the material 12 to be tested by transmitting a signal, which may be an ultrasonic wave, to the material 12 to be tested, and receiving a signal waveform, which may be altered from the transmitted signal in frequency and/or amplitude, from the material indicative of a presence of a defect in the material and a type of defect present in the material. The system 10 also may include a computer, generally designated 24, connected to the sensor 22 for receiving the signal waveform from the material 12. In an embodiment, the computer 24 may take the form of a control box 26 connected wirelessly, or by a cable, such as a USB cable 28, to a computer, which may take the form of a laptop computer, tablet, or other handheld device, generally designated 30. In another embodiment, the computer 24 may take the form of a unitary processing unit 32 that performs the combined functions of the control box 26 and laptop computer 30. The sensor 22 may receive a signal from the control box 26 or processing unit 32 to generate the transmitted signal of a predetermined amplitude and frequency, or may generate the signal in response to an instruction received from the computer 24.

As described in greater detail in U.S. patent application Ser. No. 13/977,319 filed Sep. 4, 2013 and titled METHOD AND APPARATUS FOR DEFECT DETECTION IN COMPOSITE STRUCTURES, the entire contents of which are incorporated herein by reference, the control box 26 may allow operator control of the method for inspection and defect identification of the system 10. The probe 22 may be a conventional pitch-catch probe with two transducers, one for transmitting an ultrasonic wave to the surface 34 of the material 12, and a second for receiving a reflected signal waveform from the material. The laptop computer 30, or alternatively, the processing unit 32, may include or be connected to a display 36 that receives a signal from the computer 24 to display a scanned image 38 of the test area 40.

The computer 24 may be connected to the sensor 22 wirelessly or by a cable 42 to receive a signal waveform from the sensor 22 that is reflected from the material 12. The computer 24 may include a data store that contains a table of a plurality of stored signal waveforms. Each of the stored signal waveforms corresponds to a different one of a plurality of types of defects in the material. The computer 24 is programmed to compare the received signal waveform to the plurality of stored signal waveforms, and if a match exists, assign one of a plurality of colors to the match.

For example, an area of no defect 44 may be assigned the color green, a defect caused by potting (a filled unit or units of the honeycomb core 16), may be assigned the color red 46, and a milled core defect may be assigned the color pink 48. Other defects that may be assigned different colors include a skin-to-core separation, a separation of plies within one or both skins 18, 20, and a splice in the material 12. The display 36 may include or be formed of a plurality of pixels. The display 36 may be connected to receive the signal from the computer 24 to display an assigned one of the plurality of colors at each one of the plurality of pixels, wherein each pixel corresponds to a different location on the test area 40.

In an embodiment, the software in the computer 24 may be programmed to scale the scanned image 38 such that it corresponds in size to the test area 40 in a 1:1 relationship. That way, the scanned image 38 of the test area 40 shown on the display 36 matches dimensionally with, and is the actual size of, the test area itself.

In an embodiment, the computer 24 may be programmed to change a signal waveform of the plurality of signal waveforms stored in the data store, for example, to accommodate a particular type or composition of material 12. The computer 24 also, or alternatively, may be programmed to add a signal waveform to the plurality of signal waveforms to accommodate a particular type or composition of material 12. Further, the computer 24 may be programmed to apply a changed signal waveform to a completed scan of the test area 40, and update the display of the scanned image 38.

The system 10 also may include an automated scanning platform, generally designated 50, that supports the sensor 22. The automated scanning platform 50 may move the sensor 22 in a preset or predetermined pattern or motion 52 over the surface 34 of the test area 40 of the material 12 to be tested to perform an inspection scan of the material at the test area. The scanning platform 50 may position and hold the sensor 22 at a constant, predetermined position or orientation, a constant, predetermined angle relative to the surface 34, and at a constant, predetermined contact force (for example, the contact force between the sensor 22 and the surface 34) to acquire data consistently and accurately during an inspection scan. The position, angle, and contact force may be selected to provide the optimal or most accurate readings to be taken by the sensor 22 of the material 12. Alternatively, the sensor 22 may be mounted on the scanning platform 50 by way of a universal joint, floating joint, ball joint, or other joint that allows the sensor to rotate or move relative to the scanning platform 50.

In an embodiment, the sensor 22 may include a pitch transducer 53 and a catch transducer 54. The pitch and catch transducers 53, 54, respectively, may be urged against the surface 34 of the material 12 to be tested at a constant contact force as the automated scanning platform 50 moves the sensor 22 in the predetermined motion 52 over the test area 40. In an embodiment, the automated scanning platform 50 may take the form of an encoded x-y bridge 56 with floating distal joint 57 at the sensor 22 for compliance to non-flat surfaces 34 that may be rough, wavy or arcuate, as with an aircraft wing surface. In an embodiment, polytetra-fluoroethylene (PTFE) tape may be placed over the tips of the probe tips of the pitch and catch transducers 53, 54, respectively to prevent tip wear. The computer 24 may be programmed to include stops of the sensor 22 to allow for replacement of the PTFE tape. In other embodiments, PTFE may be applied to the tips of the pitch and catch transducers 53, 54 by deposition.

The encoded x-y bridge 56 may include a transverse beam 58 and a longitudinal beam 60, the latter of which may be fixedly attached to the surface 34 of the material 12 at the test area 40 by suction cups 62, 64. The encoded x-y bridge 56 also may include a sliding nut 66 that connects the transverse beam 58 to the longitudinal beam 60 for slidable relative movement. The end of the transverse beam 58 opposite the sliding nut 66 may be connected to a support foot 68 that extends downwardly to contact the surface 34 of the material 12. The height of the sensor 22 thus may be maintained at a precise distance from the surface 34 of the material 12 at all times that the sensor 22 is moved along the preset motion 52.

In an embodiment, the automated scanning platform 50 may position the sensor 22 at a constant angle relative to the surface 34 of the test area 40 during the preset motion of the inspection scan 52 over the test area. In an embodiment, the automated scanning platform 50 may position the sensor 22 normal to the surface 34 in the preset motion of the inspection scan 52 over the test area 40. The scanning platform 50 may position the sensor 22 normal to the surface 34 at all times in the preset motion of the inspection scan 52 over the test area 40. This feature may require that the sensor 22 be attached to the scanning platform 50 by a distal joint 57 that takes the form of a gimbaled mount. Also in an embodiment, the automated scanning platform 50 may urge the sensor 22 against the surface 34 at a constant contact force in the preset motion of the inspection scan 52 over the test area 40. In the embodiment of FIG. 1, the pitch and catch transducers 53, 54 may be urged at a constant contact force against the surface 34 of the material 12. Also in an embodiment, the computer 24 may be programmed to move the sensor at a constant, predetermined speed over the surface 34 of the 14 of the material 12, and also preferably at a constant direction.

Figure 2:
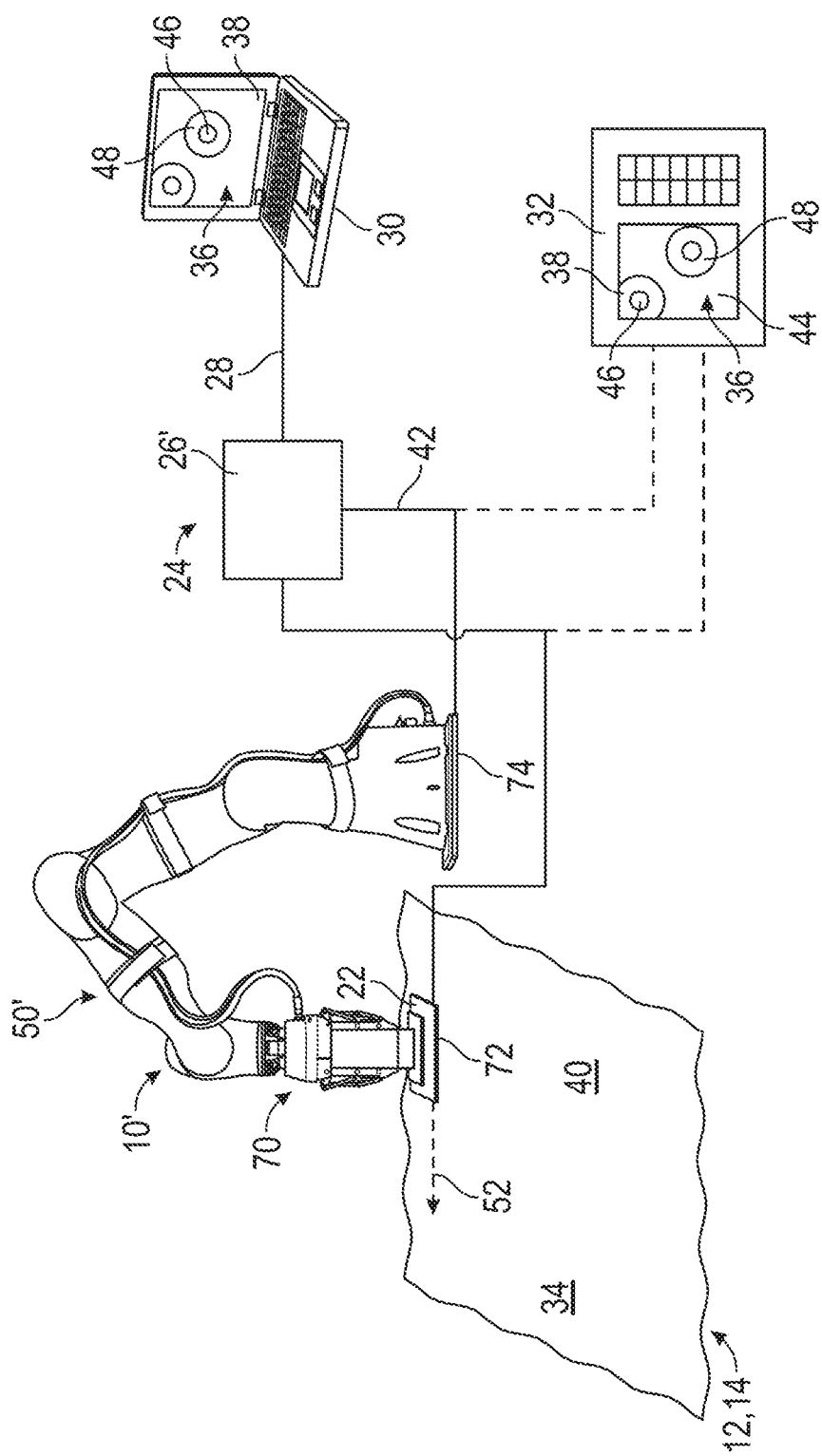
FIG. 2 is a schematic, perspective view of another embodiment of the system and method for automated bond testing.

As shown in FIG. 2, in another embodiment 10' of the disclosed system for automated bond testing, a scanning platform 50' may take the form of an articulated robot arm 70. For example, the robot arm 70 may have seven axes of movement be mounted on a base 74 that may be positioned adjacent the test area 40 of the material 12 to be tested. An example of such a robot arm 70 is the KUKA model LBR iiwa 7 R800 manufactured by KUKA Roboter GmbH of Augsburg, Germany. Such a robot arm 70 may include torque sensors in all seven axes, which provide the robot with contact detection capabilities and programmable compliance. An advantage of using the articulated robot arm 70 is that the base 74 of the robot arm 70 may be positioned on the material remotely from the test area 40, or on a support not on the vehicle containing the panel 14, so that the presence of the scanning platform 50' does not dampen the vibrations emitted by the sensor 22.

The robot arm 70 may be controlled by a controller 26' that may be programmed and/or operated by a computer 24, such as a laptop 30, connected to the controller by a USB cable 28. The controller 26' may be connected to the robot arm 70 by a cable 42. The controller 26' may be programmed by the laptop 30, or contain loaded software that actuates the robot arm 70 to move the end effector 72 that consists of or contains the sensor 22 along the inspection scan 52 on the surface 34 of the test area 40 of the material to be tested 12. The robot arm 70 may be capable of moving the sensor 22 in three dimensions (along an x axis, a y axis, and a vertical z axis) to accommodate a three-dimensional surface 34 of the test area 40. The software contained in the computer 24 (in the controller 26' and/or the laptop 30) controls the robot arm 70 to move the sensor 22 to accommodate deviations from flatness of the surface 34 and at the same time maintain a constant contact force between the transducers 53, 54 (FIG. 1) and the surface 34 over the test area 40 and at all times during the inspection scan 52.

Alternately, the system 10' of FIG. 2 may include a computer 24 in the form of a unitary processing unit 32 having a display 36. The processing unit 32 also may include a controller for the robot arm 70, or alternately be connected to the controller 26' to operate the robot arm. In addition, the unit 32 may be connected to the sensor 22 to receive a signal waveform from the sensor 22 that is received from the material 12.

Figure 3:
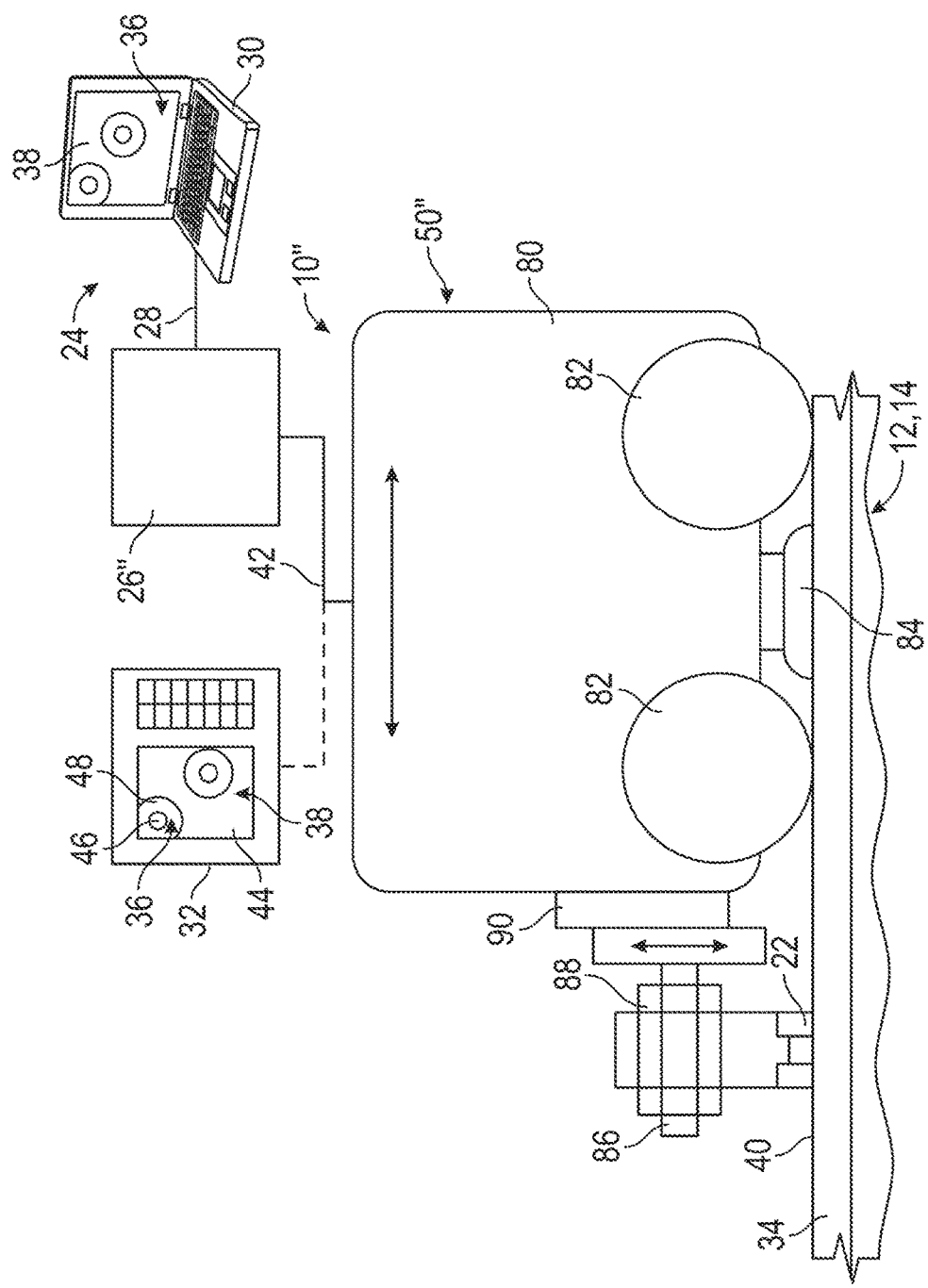
FIG. 3 is a detail of yet another embodiment of the system and method for automated bond testing.

As shown in FIG. 3, in yet another embodiment 10" of the system for automated bond testing, the automated scanning platform 50" may include a crawling robot 80. The crawling robot 80 may be remotely controlled by a computer 24 that includes a controller 26" that is actuated by a laptop computer 30 connected wirelessly or by a USB cable 28. The controller may be connected by a cable 42 to the crawling robot 80, or alternately, there may be a wireless connection, such as a Bluetooth or Wi-fi connection. As in the embodiments of FIGS. 1 and 2, alternately, the system 10" may include a processing unit 32 that performs the functions of the controller 26" and the laptop 30 to control the operation of the crawling robot 80 and also displays the scanned image 38 taken of the surface 34 of the test area 40 showing defects 46, 48, for example, on a display 36.

The crawling robot 80 may include four wheels 82 (only two of which are shown) that are powered by an on-board electric motor and remotely actuated by the controller 26", and a suction mount 84 that may be selectively actuated to fix and hold the robot 80 in place on the surface 34 to take a reading by the sensor 22.

The sensor 22 may be mounted on an x-axis stage 86 that moves the sensor 22 laterally relative to the crawling robot 80 (that is, into and out of the plane of the drawing FIG. 3), a gimbaled mount 88 that allows the sensor to be aligned to the surface 34 of the test area 40, and a slide 90 that may be actuated to move the sensor 22 vertically along a z axis to accommodate changes in surface elevation relative to the crawling robot 80. The x-axis stage 86, the gimbaled mount 88, and the slide 90 all may be actuated by the computer 24 to maintain the sensor 22 at a preset orientation, angle to the surface 34 (e.g., normal to the surface), and at a preset contact force against the surface. Alternatively, the robot crawler 80 may have its own program for actuating these components and maintaining these orientations of the sensor 22.

Figure 4:
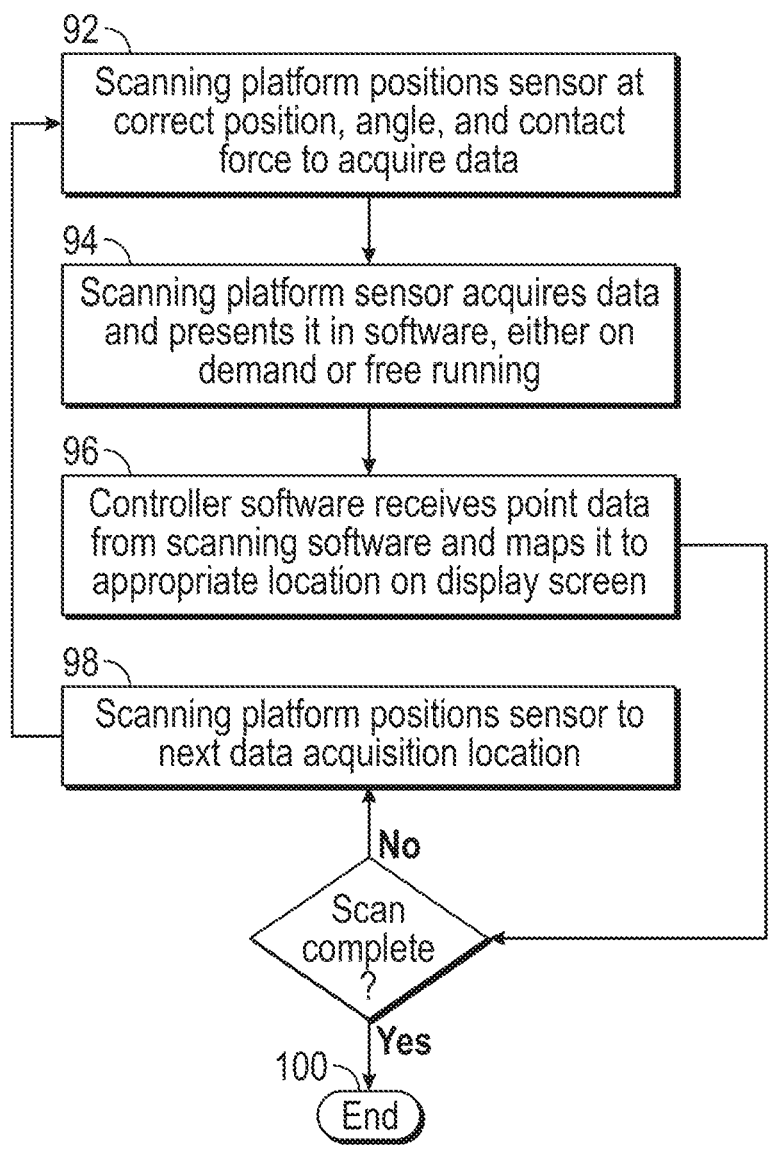
FIG. 4 is a flow chart of the software used in the embodiments of FIGS. 1, 2, and 3.

As shown in FIG. 4, the method of operation of the system for automated bond testing 10, 10', 10" begins with the scanning platform 50 being actuated by the computer 24 to position the sensor 22 at the correct position, angle, and contact force on the surface 34 of the test area 40 of the material 12 to acquire data, as indicated in block 92. Next, as indicated in block 94, the computer 24 may actuate the scanning platform sensor 22 to acquire data and present it in software, either on demand or as part of a free running scanning program loaded into the computer 24.

In particular, the computer 24 may actuate the sensor 22 to transmit an ultrasonic signal from pitch transducer 53 downwardly through the surface 34 and into the material 12 at the test area, and then receive a reflected signal waveform through catch transducer 54. That signal is then received by the controller 26, 26', 26", or received in unitary processing unit 32, which incorporates the controller, where it is processed by the software to compare the signal waveform received from the sensor 22 to a table of stored waveforms to determine whether a defect is present at the location of the sensor 22. As indicated in block 96, the software in the controller receives this point data from the scanning software, and maps it to an appropriate location on the display screen 36 of the laptop 30, or alternately the unit 32.

Next, as indicated in block 98, the scanning platform 50, 50', 50" may position the sensor 22 to a next data acquisition location along the inspection scan path 52 in the test area 40 of the material 12. The process described in blocks 92, 94, 96 may be repeated at the next successive data acquisition location until the scan is complete. After the scanning platform 50, 50', 50" has incrementally moved the sensor through the path 52 of the inspection scan, the scanning program may terminate, as indicated at block 100. At that point, the display 36 contains a scanned image 38 of the test area 40 that has been traversed by the sensor 22, having been moved by the scanning platform 50, 50', 50". This scanned image 38 may be studied, may be stored, and/or may be transmitted, either over a network or wirelessly for further study and/or storage.

The system and method for automated bond testing disclosed herein also may include a method for using the automated bond testing system 10, 10', 10". The method for testing bonds in composite materials may include mounting on an automated scanning platform 50, 50', 50" a sensor 22 sending and receiving a signal waveform. The automated scanning platform 50, 50', 50" is activated such that the scanning platform moves the 22 sensor in a preset motion over a test area 40 of the material to be tested 12 to perform a scan of the material. The preset motion may include orienting the sensor 22 at a predetermined position, a predetermined angle, and a predetermined contact force with the material 12 to acquire data consistently during the inspection. A signal may be sent to the material to be tested 12 and the sensor 22 may receive a signal waveform from the material indicative of a presence of a defect in the material.

The signal waveform may be received from the sensor 22 at a computer 24 configured to have access to a plurality of signal waveforms, each of the signal waveforms corresponding to a different one of a plurality of types of defects in the material, and to compare the received signal waveform to the plurality of signal waveforms. If a match exists, one of a plurality of colors is assigned to the match. A signal is sent from the computer 24 to a display 36, the display showing an image of the test area on the material to be tested 12 having an assigned one of the plurality of colors indicative of a presence or absence of a defect in the test area.

The method for automated bond testing disclosed herein also may include a method for making an automated bond testing system 10, 10', 10". The method may begin with mounting on an automated scanning platform 50 a sensor 22 that is capable of scanning a material 12 to be tested by sending a signal to the material to be tested and receiving a signal waveform from the material indicative of a presence of a defect in the material. The scanning platform 50 is configured and is capable of moving the sensor in a preset motion over a test area 40 of the material 12 to be tested to perform a scan of the material.

A computer 24 may be connected to the sensor 22 over a cable 42 to receive a signal waveform from the sensor collected and received from the material 12. The computer 24 is programmed to include a table of a plurality of stored signal waveforms, each of the stored signal waveforms corresponding to a different one of a plurality of types of defects of the stored signal waveforms corresponding to a different one of a plurality of types of defects in the material 12. The programming further may enable the computer 24 to compare the signal waveform received from the sensor 22 to the plurality of stored signal waveforms, and if a match exists, to assign one of a plurality of colors to the match.

The computer 24 may be connected to, or include, a display 36 that receives a signal from the computer to display a scanned image 38 of the test area 40 having an assigned one of the plurality of colors indicative of a presence or absence of a defect in the test area. The automated scanning platform 50 may be further programmed to move the sensor 22 in a preset motion 52 over a surface 34 of a test area 40, and to position the sensor at a predetermined position relative to the surface 34 at a predetermined angle to the surface 34, and at a predetermined contact force to acquire data consistently during an inspection scan.

In a particular embodiment, the automated scanning platform 50 may be directed by the computer 24 to perform a scanning operation during which the sensor 22 is positioned at a constant angle relative to the surface 34 of the test area 40 during the preset motion 52 of the inspection scan over the test area. And in a particular embodiment, the constant angle may be one in which the sensor 22 is normal to the surface 34 at all times during the preset motion 52 of the inspection scan over the test area 40. Similarly, in a particular embodiment, the automated scanning platform is actuated by the computer 24 to urge the sensor 22 against the surface 34 at a constant contact force at all times during the preset motion 52 of the inspection scan over the test area 40. Further, the scanning platform 50 may be actuated by the computer 24 to move the sensor 22 in three dimensions, namely an x, y and z (vertical) dimension to conform the sensor 22 to the surface 34 during the preset motion 52 of the inspection scan over the test area 40.

In various embodiments, the scanning platform 50, which may take the form of an encoded x-y bridge 58, a robot arm 70, and a crawling robot 80, may itself be programmed to traverse the test area 40 and during the traversal, position the sensor 22 at the appropriate angle, and pressure to maintain a constant orientation and force against the surface 34.

Alternately, the scanning platform may include tactile sensors that detect a change in elevation or deviation from flatness of the surface 34 to be tested, and react accordingly by repositioning the sensor 22. As a result, the disclosed system and method for automated bond testing 10, 10', 10", may be capable of providing a high precision two-dimensional display of a scanned image 38 taken from a three-dimensional test area 40 on a material 12 to be tested.

While the disclosed forms of apparatus and methods constitute preferred embodiments of the system and method for automated bond testing, it is to be understood that the scope of the invention is not limited to these precise methods and systems, and that changes may be made therein without departing from the scope of the invention.

What is claimed is:

1. A system for automated bond testing, the system comprising:
    a sensor that scans a material to be tested by sending a signal to the material to be tested and receiving a signal waveform from the material indicative of a presence of a defect in the material and a type of defect present in the material;
    a computer in communication with the sensor for receiving the signal waveform from the material, the computer being configured to compare the received signal waveform to a plurality of signal waveforms indicating a defect in the material, and if a match exists, assign a one of a plurality of colors to the match;
    a display connected to receive a signal from the computer to display an image of the material to be tested having an assigned one of the plurality of colors indicative of a presence or absence of a defect in the test area; and
    an automated scanning platform that supports the sensor, the scanning platform moving the sensor in a preset motion over a surface of a test area of the material to be tested to perform an inspection scan of the material at the test area, and that positions the sensor at a predetermined position, a predetermined angle, and a predetermined contact force to acquire data consistently during an inspection.

2. The system of claim 1, wherein the automated scanning platform positions the sensor at a constant angle relative to the surface of the test area during the preset motion of the inspection scan over the test area.

3. The system of claim 2, wherein the automated scanning platform positions the sensor normal to the surface in the preset motion of the inspection scan over the test area.

4. The system of claim 3, wherein the automated scanning platform positions the sensor normal to the surface at all times in the preset motion of the inspection scan over the test area.

5. The system of claim 1, wherein the automated scanning platform urges the sensor against the surface at a constant contact force in the preset motion of the inspection scan over the test area.

6. The system of claim 1, wherein the automated scanning platform moves the sensor in three dimensions to conform to the surface in the preset motion of the inspection scan over the test area, to maintain the sensor at a constant angle relative to the surface and to maintain the sensor at a constant contact force relative to the surface in the preset motion of the inspection scan over the test area.

7. The system of claim 1, wherein the automated scanning platform is selected from a crawler, an articulated robot arm, and an encoded x-y bridge.

8. The system of claim 1, wherein the computer is programmed to perform one or both of changing or adding a signal waveform of the plurality of signal waveforms, apply the changed signal waveform to a completed scan of the test area, and update a display of the scanned image.

9. The system of claim 1, wherein the display includes a plurality of pixels; and the display is connected to receive the signal from the computer to display an assigned one of the plurality of colors at each one of the plurality of pixels, wherein each pixel corresponds to a different location on the test area.

10. The system of claim 9, wherein the display shows a plurality of different defects in the test area of the material, and each type of the plurality of different defects is displayed in a different color.

11. The system of claim 1, wherein the material includes a honeycomb core joined to upper and lower skins; and the defects are selected from a skin-to-core separation, a separation of plies within the skin, a splice in the material, and a potted core.

12. A method for testing bonds in composite materials, the method comprising:
    mounting on an automated scanning platform a sensor sending and receiving a signal waveform;
    activating the automated scanning platform such that the scanning platform moves the sensor in a preset motion over a test area of the material to perform a scan of the material;
    the preset motion including a predetermined position, at a predetermined angle, and a predetermined contact force to acquire data consistently during an inspection;
    sending a signal to the material to be tested and receiving a signal waveform from the material indicative of a presence of a defect in the material;
    receiving the signal waveform at a computer configured to have access to a plurality of signal waveforms, each of the signal waveforms corresponding to a different one of a plurality of types of defects in the material, and to compare the received signal waveform to the plurality of signal waveforms, and if a match exists, assign one of a plurality of colors to the match; and
    sending a signal from the computer to a display, the display showing an image of the test area on the material to be tested having an assigned one of a plurality of colors indicative of a presence or absence of a defect in the test area.

13. The method of claim 12, wherein the material to be tested is a composite panel on an aircraft.

14. The method of claim 12, wherein activating the automated scanning platform includes positioning the sensor normal to the surface at all times, at a constant contact force, and in three dimensions to conform to the surface in the preset motion of the inspection scan over the test area in the preset motion of the inspection scan over the test area.

15. The method of claim 12, wherein activating the automated scanning platform includes moving the sensor at a constant scanning speed over the test area.

16. The method of claim 15, wherein programming the automated scanning platform includes programming the automated scanning platform to position the sensor at a constant angle relative to the surface of the test area during the preset motion of the inspection scan over the test area.

17. The method of claim 16, wherein programming the automated scanning platform includes programming the automated scanning platform to position the sensor normal to the surface at all times during the preset motion of the inspection scan over the test area.

18. A method for making an automated bond testing system, the method comprising:

mounting on an automated scanning platform a sensor that scans a material to be tested by sending a signal to the material to be tested and receiving a signal waveform from the material indicative of a presence of a defect in the material, the scanning platform moves the sensor in a preset motion over a test area of the material to be tested to perform a scan of the material;

connecting a computer to the sensor for receiving the signal waveform from the material;

programming the computer to have a table of a plurality of stored signal waveforms, each of the stored signal waveforms corresponding to a different one of a plurality of types of defects in the material, and to compare the received signal waveform to the plurality of stored signal waveforms, and if a match exists, assign one of a plurality of colors to the match;

connecting a display to receive a signal from the computer to display a scanned image of a test area on the material to be tested having an assigned one of the plurality of colors indicative of a presence or absence of a defect in the test area; and programming the automated scanning platform to move the sensor in a preset motion over a surface of a test area of the material to be tested to perform an inspection scan of the material at the test area, and to position the sensor at a predetermined position, a predetermined angle, and a predetermined contact force to acquire data consistently during an inspection.

19. The method of claim 18, wherein programming the automated scanning platform includes programming the automated scanning platform to urge the sensor against the surface at a constant contact force at all times during the preset motion of the inspection scan over the test area.

20. The method of claim 18, wherein programming the automated scanning platform includes programming the automated scanning platform to move the sensor in three dimensions to conform to the surface in the preset motion of the inspection scan over the test area.

\* \* \* \* \*

UNITED STATES PATENT AND TRADEMARK OFFICE
CERTIFICATE OF CORRECTION

| | | |
|---|---|---|
| PATENT NO. | : 9,594,059 B1 | |
| APPLICATION NO. | : 14/985646 | |
| DATED | : March 14, 2017 | |
| INVENTOR(S) | : Steven K. Brady et al. | |

It is certified that error appears in the above-identified patent and that said Letters Patent is hereby corrected as shown below:

In the Claims

Claim 14, Column 10, Lines 52-53 read:

"preset motion of the inspection scan over the test area in the preset motion of the inspection scan over the test area."

It should read:

--preset motion of the inspection scan over the test area.--

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*